United States Patent
Kojima et al.

(10) Patent No.: US 12,419,545 B2
(45) Date of Patent: Sep. 23, 2025

(54) RESPIRATION INFORMATION ESTIMATION DEVICE AND RESPIRATION INFORMATION ESTIMATION METHOD

(71) Applicant: Mitsubishi Electric Corporation, Tokyo (JP)

(72) Inventors: Taichi Kojima, Tokyo (JP); Yudai Nakamura, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 401 days.

(21) Appl. No.: 17/923,600

(22) PCT Filed: Jun. 2, 2020

(86) PCT No.: PCT/JP2020/021766
§ 371 (c)(1),
(2) Date: Nov. 7, 2022

(87) PCT Pub. No.: WO2021/245787
PCT Pub. Date: Dec. 9, 2021

(65) Prior Publication Data
US 2023/0200684 A1    Jun. 29, 2023

(51) Int. Cl.
*A61B 5/11*    (2006.01)
*A61B 5/00*    (2006.01)
(Continued)

(52) U.S. Cl.
CPC .......... *A61B 5/1128* (2013.01); *A61B 5/0077* (2013.01); *A61B 5/113* (2013.01); *G06T 7/0012* (2013.01); *G06T 2207/10016* (2013.01)

(58) Field of Classification Search
None
See application file for complete search history.

(56) References Cited

U.S. PATENT DOCUMENTS 9,861,302 B1    1/2018  Chatterjee et al.
2016/0100766 A1*  4/2016  Yoshioka ............. A61B 5/0082
                                                       600/301
(Continued)

FOREIGN PATENT DOCUMENTS

JP    2011-130996 A    7/2011

OTHER PUBLICATIONS

International Search Report and Written Opinion mailed on Aug. 25, 2020, received for PCT Application PCT/JP2020/021766, filed on Jun. 2, 2020, 9 pages including English Translation.

(Continued)

*Primary Examiner* — Mark R Milia
(74) *Attorney, Agent, or Firm* — XSENSUS LLP

(57) ABSTRACT

A respiration information estimation device includes a specific region setting unit that sets a specific region and a motion vector calculation point as a point as a reference of a motion vector based on an image including an upper body of an object person, a motion vector calculation unit that calculates the motion vector from a movement amount of the motion vector calculation point in each of the images captured consecutively, a respiration reference axis calculation unit that calculates a respiration reference axis from a respiration central point and the motion vector calculation point, a respiration signal calculation unit that calculates a respiration signal from a component of the motion vector in a direction of the respiration reference axis, and a respiration information calculation unit that calculates a respiration information estimation result, as a result of estimating a body motion caused by the respiration, from the respiration signal.

11 Claims, 13 Drawing Sheets

(51) Int. Cl.
    *A61B 5/113*     (2006.01)
    *G06T 7/00*     (2017.01)

(56) References Cited

U.S. PATENT DOCUMENTS

2018/0000382 A1    1/2018   Chatterjee et al.
2019/0209046 A1*   7/2019   Addison ............. A61B 5/1135

OTHER PUBLICATIONS

Chatterjee et al., "Real-time Respiration Rate Measurement from Thoracoabdominal Movement with a Consumer Grade Camera", IEEE, 2016, pp. 2708-2711.
Chatterjee et al., "Real-time Visual Respiration Rate Estimation with Automatic Scene Adaptation", 2016 IEEE 16th International Conference on Bioinformatics and Bioengineering, IEEE Computer Society, 2016, pp. 154-160.
Office Action issued on Jun. 20, 2025 in counterpart Chinese Patent Application No. 202080101274.3 (17 pages; with English translation).

* cited by examiner

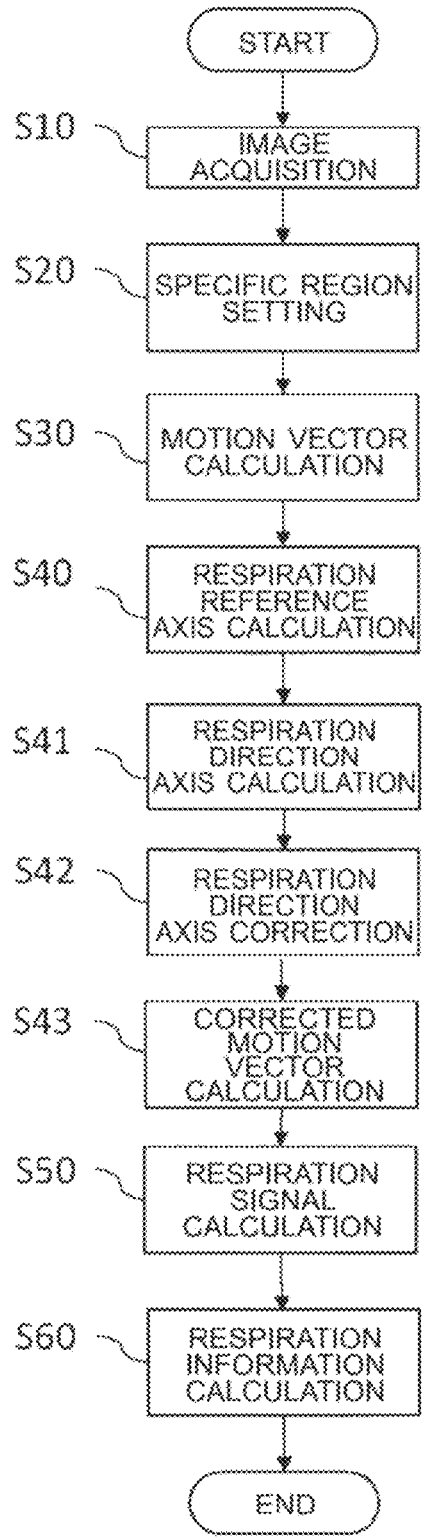

FIG. 17
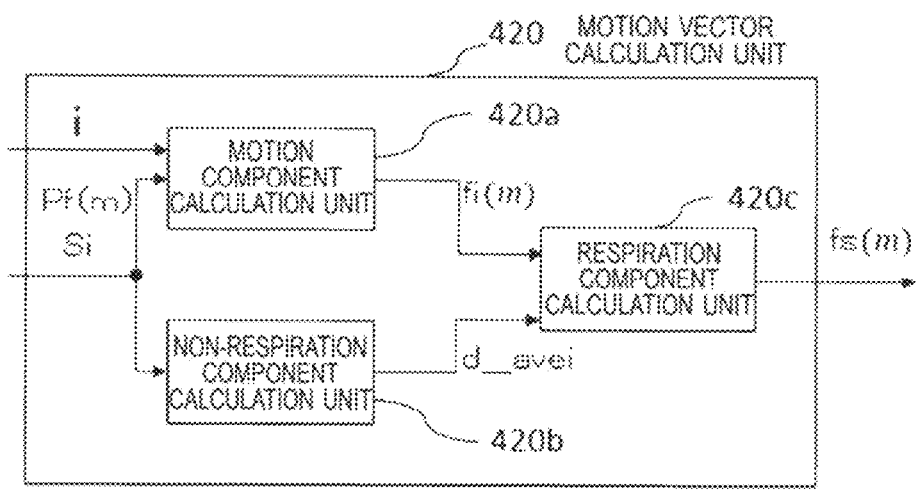
FIG. 18(a)   FIG. 18(b)   FIG. 18(c)
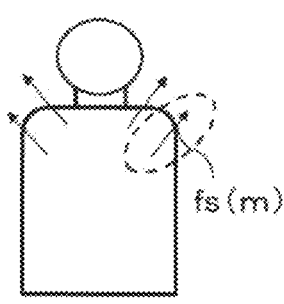
DESIRED RESPIRATION
COMPONENT fs(m)
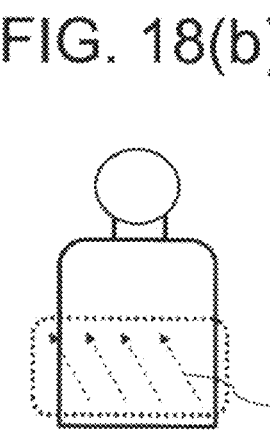
NON-RESPIRATION
COMPONENT d_avei
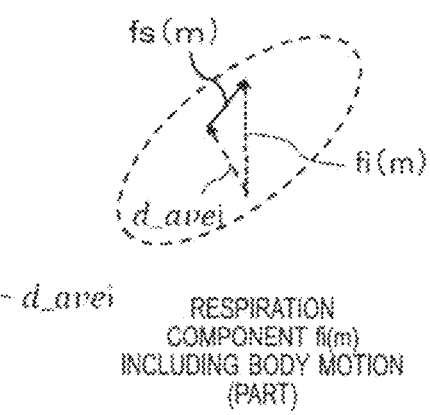
RESPIRATION
COMPONENT fi(m)
INCLUDING BODY MOTION
(PART)

RESPIRATION INFORMATION ESTIMATION DEVICE AND RESPIRATION INFORMATION ESTIMATION METHOD

CROSS-REFERENCE TO RELATED APPLICATION

The present application is based on PCT filing PCT/JP2020/021766, filed Jun. 2, 2020, the entire contents of which are incorporated herein by reference.

TECHNICAL FIELD

The present disclosure relates to a respiration information estimation device and a respiration information estimation method for measuring respiration information on an object person in a non-contact manner.

BACKGROUND ART

In recent years, an object person can grasp the person's own health condition in a simple manner just by wearing a wearable terminal such as a smartwatch, without going to a hospital. However, that requires the object person to constantly wear the wearable terminal in daily life and the burden on the object person is heavy.

Among various biological signals, respiration is drawing attention as a biological signal that can be consciously controlled by oneself, unlike pulsation and the like. For example, a respiration method like yoga is known to be able to make the parasympathetic nerve dominant and relax mind and body, and thus it is expected to use respiration as one application for controlling the health condition. There is a method for measuring respiration: when an object person wraps a belt-type sensor around the breast or the abdomen, a motion of the breast or the abdomen due to the respiration causes the belt-type sensor to expand and contract, and respiration can be measured based on the change in the inductance. However, wearing such a sensor for a long time becomes a burden on the object person as mentioned above.

As a method not imposing a burden on the object person, it can be considered to measure the respiration in a non-contact manner. As a technique for measuring the respiration in a non-contact manner, there has been known a technology of estimating respiration information on the object person from captured images of the object person and there has been disclosed a technology of estimating the respiration information by capturing images of the upper body of the object person in a resting state and detecting a motion of the upper body caused by the respiration (see Patent Reference 1, for example).

In the above-described technology, it is a precondition that the measurement is taken when the object person is in the resting state. Based on captured images over a constant period, a respiration direction axis representing a particular motion direction of the upper body due to the respiration is obtained and a respiration waveform is calculated by correcting measurement data by removing a body motion component based on the respiration direction axis.

PRIOR ART REFERENCE

Patent Reference

Patent Reference 1: U.S. Pat. No. 9,861,302

SUMMARY OF THE INVENTION

Problem to be Solved by the Invention

However, the conventional technology has a problem in that a correct respiration direction axis cannot be obtained and the accuracy decreases when a body motion not caused by the respiration occurs in the constant period even though the correct respiration direction axis can be calculated if the object person is in the resting state.

For example, in cases where the measurement is taken when the object person is riding on a vehicle, it is easily presumed that there is a body motion not caused by the respiration such as a motion of the driver's upper body caused by vibration of the vehicle, and thus it is necessary to estimate the respiration with high accuracy even when the upper body of the object person moves during the measurement.

It is therefore an object of the present disclosure to make it possible to estimate the respiration information with high accuracy even when there is a body motion not caused by the respiration in a constant period.

Means for Solving the Problem

A respiration information estimation device according to the present disclosure includes a specific region setting unit that sets a specific region and a motion vector calculation point as a point as a reference of a motion vector based on an image including an upper body of an object person, a respiration reference axis calculation unit that calculates a respiration reference axis from a respiration central point as a starting point of a motion caused by respiration and the motion vector calculation point, a motion vector calculation unit that calculates the motion vector from a movement amount of the motion vector calculation point in each of the images captured consecutively, a respiration signal calculation unit that calculates a respiration signal from a component of the motion vector in a direction of the respiration reference axis, and a respiration information calculation unit that calculates a respiration information estimation result, as a result of estimating a body motion caused by the respiration, from the respiration signal.

Effect of the Invention

According to the present disclosure, by using the respiration reference axis as the reference of the respiration calculated from the specific region of the object person, the respiration information on the object person can be estimated with high accuracy even when there is a body motion not caused by the respiration in a constant period.

BRIEF DESCRIPTION OF THE DRAWINGS

FIG. 15 is a flowchart showing the operation of the respiration information estimation device in the second embodiment.

FIG. 17 is a block diagram schematically showing the configuration of a motion vector calculation unit in the third embodiment.

FIGS. 18(a), 18(b) and 18(c) are schematic diagrams showing a method of removing a non-respiration component from the motion vector in the third embodiment.

MODE FOR CARRYING OUT THE INVENTION

First Embodiment

Figure 1:
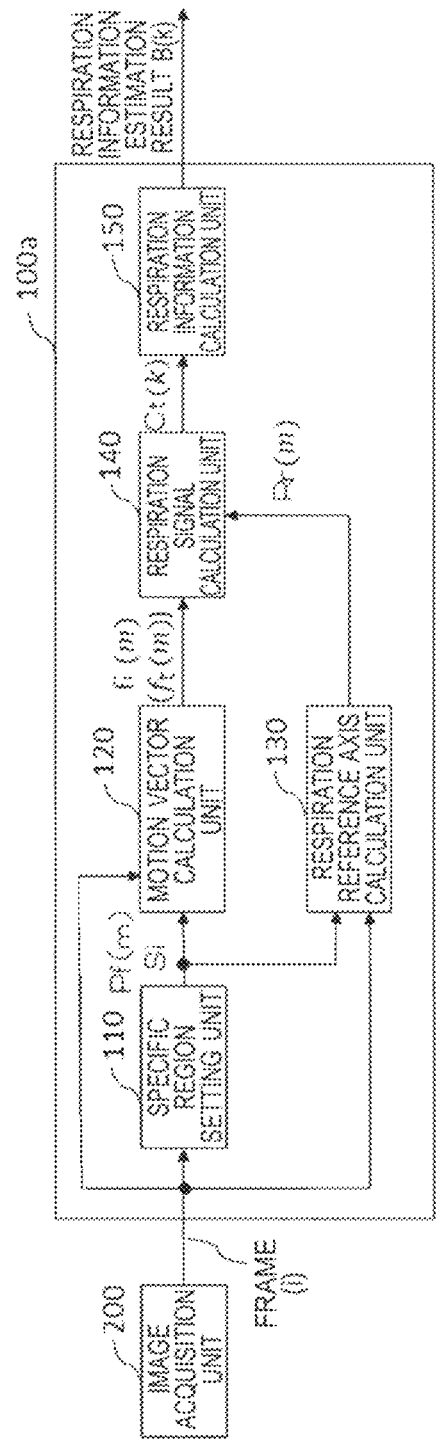
FIG. 1 is a block diagram schematically showing the configuration of a respiration information estimation device in a first embodiment.

FIG. 1 is a block diagram schematically showing the configuration of a respiration information estimation device 100a according to a first embodiment. The respiration information estimation device 100a is a device that executes a respiration information estimation method according to the first embodiment. As shown in FIG. 1, the respiration information estimation device 100a is connected to an image acquisition unit 200 and includes a specific region setting unit 110, a motion vector calculation unit 120, a respiration reference axis calculation unit 130, a respiration signal calculation unit 140 and a respiration information calculation unit 150.

First, the general outline of the respiration information estimation device 100a will be described below. The respiration information estimation device 100a receives an input of image data of video including a total of N frames captured by the image acquisition unit 200 at a predetermined frame rate r. Here, N is an integer greater than or equal to 2. Let i (i=1, 2, N) represent a frame number assigned to each frame, a frame that is given next to a frame (i) is a frame (i+1). When a predetermined time t1 is reached, the respiration information estimation device 100a acquires image data from the image data of N frames and outputs a respiration information estimation result B(k) obtained by estimating a body motion caused by respiration. Here, the argument k is an output number that is updated after the predetermined time t1 is reached. For example, next to the respiration information estimation result B(k), the respiration information estimation device 100a outputs a respiration information estimation result B(k+1) as the result of the next respiration information estimation.

Here, i representing the frame number and k representing the output number are integers greater than or equal to 1. The frame rate r may be set in consideration of a microcomputer's processing speed, an image size, etc., for example, and is assumed to be 30 frames per second in this embodiment. Further, the number N of frames used for outputting the respiration information estimation result B(k) is assumed to be an arbitrary numerical value. Here, by setting the predetermined time t1 so that t1×r exactly equals N, all of the image data that can be acquired during the time t1 can be handled. For example, the number N of frames used for outputting the respiration information estimation result B(k) is a number of frames corresponding to 10 seconds, that is, 300 frames in the above-described example. Since the number of respirations in 10 seconds is generally three times or so, t1 is set at 10 seconds and N is set at 300 in consideration of the time from the accumulation of data to the presentation of the respiration information estimation result B(k) to a user. In this case, the argument k is updated every second after the predetermined time t1 is reached, for example. The respiration information estimation result B(k+1) uses data of 300 frames, from the data of the 31st frame to the data of the 330th frame. Incidentally, the number of object persons as persons included in the image data may be either one or a plural number. To simplify the description, the number of object persons included in the image data is assumed to be one in the following description.

The image represented by the image data may be either a grayscale image, an Red Green Blue (RGB) image, an infrared (IR) image or a distance image having distance information indicating the distance to the object person as long as the upper body of the object person is captured in the image. Here, to simplify the description, a case of grayscale images will be described below. Further, the image data may be either two-dimensional data or three-dimensional data. To simplify the description, a case where the image data is two-dimensional data will be described below. In this case, the image data is formed with Nx pixels in the horizontal direction and Ny pixels in the vertical direction, for example. Nx and Ny are integers greater than or equal to 1. Incidentally, the image acquisition unit 200 may employ Charge Coupled Devices (CCDs), for example, and is arranged at a position where the upper body of the object person can be captured in the image. For example, the image acquisition unit 200 is arranged to photograph the object person from a direction squarely facing the object person's body when the object person's body is facing forward. Alternatively, the image acquisition unit 200 may be arranged to photograph the object person from the side when the object person's body is facing forward.

The components forming the respiration information estimation device 100a will be described below. The specific region setting unit 110 sets a specific region Si including the upper body of the object person based on the frame (i) included in the image data inputted from the image acquisition unit 200.

The specific region Si in the first embodiment is assumed to be a region corresponding to the breast of the object person in the following description. However, the specific region Si can also be a region other than the breast of the object person. For example, the specific region Si can be a region where a motion caused by the respiration is detected, such as a shoulder or the abdomen. Incidentally, the specific region Si can be a plurality of regions. Further, the specific region Si may be formed of either one point or a plurality of points.

The method of setting the specific region Si can be either a method of setting the specific region Si based on a face detection result or a method of setting the specific region Si based on a skeletal structure detection result including skeletal structure information regarding a person's shoulder, elbow and the like. Alternatively, the method of setting the specific region Si can be Active Appearance Models (AAM) in which the specific region Si is extracted by fitting a model on the object person. In the following, a case of using the method of setting the specific region Si based on the face detection result will be described. Further, the specific region Si is represented by using a coordinate system in the frame (i), in which a top left point in the frame (i) is defined as the origin, a rightward direction in the frame (i) is defined as a +x-axis direction, and a downward direction in the frame (i) is defined as a +y-axis direction.

Figure 2:
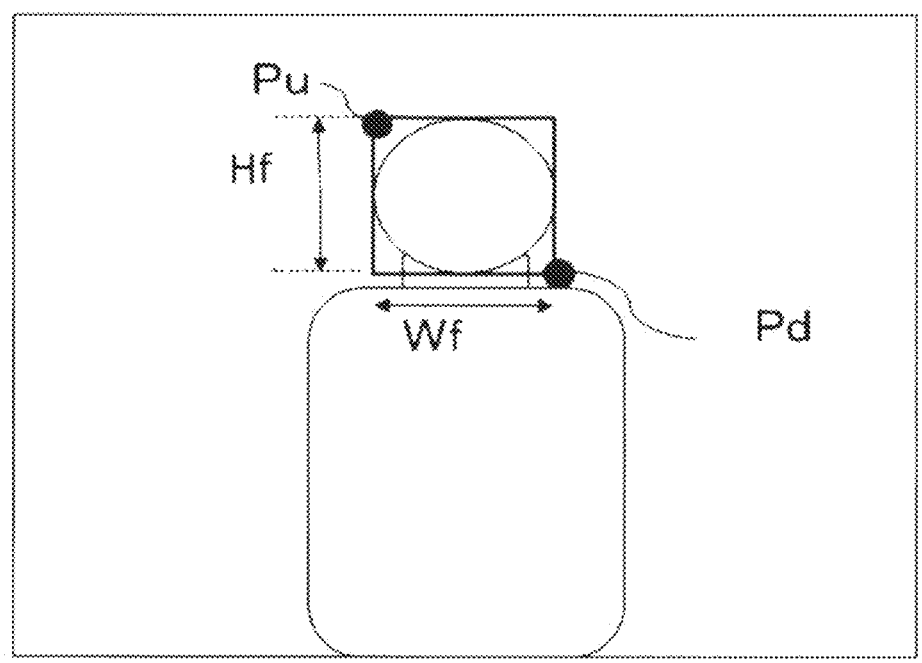
FIG. 2 is an explanatory diagram showing a face detection result.
Figure 3:
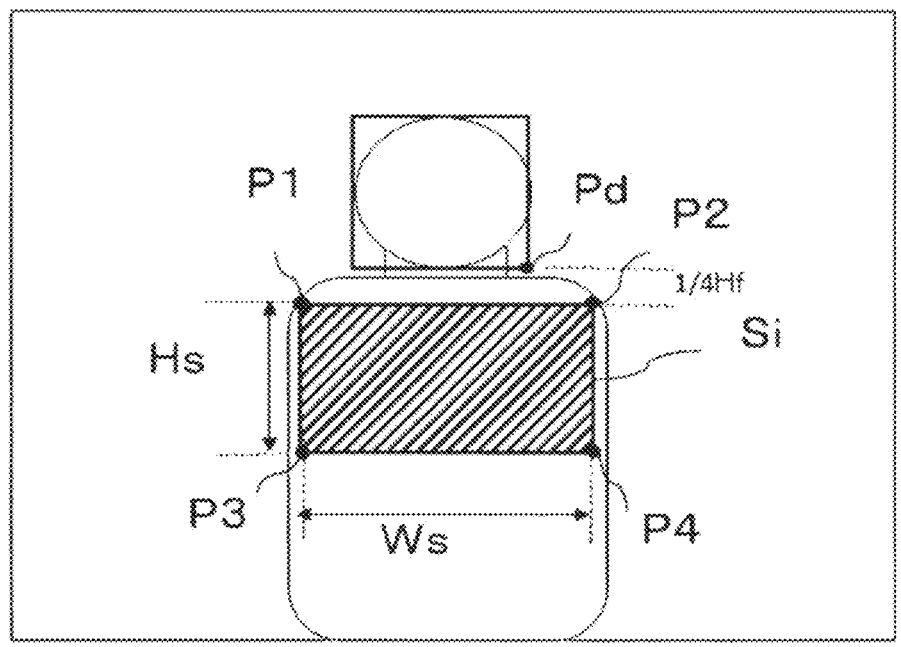
FIG. 3 is an explanatory diagram showing a specific region.

FIG. 2 is an explanatory diagram showing the face detection result. FIG. 3 is an explanatory diagram showing the specific region. In the image in the frame (i) like the one shown in FIG. 2 acquired by the image acquisition unit, a face region is detected from the upper body of the object person. For the detection of the face region, a technique like the Haar-like feature value is used, for example. The specific region setting unit 110 detects a quadrangular region as the face region. For example, it is assumed that the quadrangular region represented as its top left point Pu and its bottom right point Pd is obtained as a face region detection result. Subsequently, the specific region setting unit 110 calculates a face height Hf and a face width Wf of the object person from the top left point Pu of the quadrangular region and the bottom right point Pd of the quadrangular region. Further, the specific region setting unit 110 relatively calculates a height Hs of the specific region Si, a width Ws of the specific region Si and a position of the specific region Si from the calculated face height Hf and face width Wf. For example, the specific region Si becomes larger with the increase in the face height Hf and the face width Wf, and the specific region Si becomes smaller with the decrease in the face height Hf and the face width Wf. For example, as shown in FIG. 3, a position below a position that is ¼ face height Hf downward from the bottom right point Pd of the quadrangular region is regarded as the position of the specific region. Si in consideration of the length of the neck. For example, the height Hs of the specific region Si is set at the same value as the face height Hf of the object person, and the width Ws of the specific region Si is set at twice the face width Wf of the object person. Based on the height Hs of the specific region Si and the width Ws of the specific region Si, the specific region setting unit 110 sets four apices (P1, P2, P3, P4) surrounding the specific region Si.

The specific region setting unit 110 may reset the specific region Si when an apex of the specific region Si has moved for a distance greater than or equal to a previously set threshold value, or moved to the outside of the frame, between the image of the frame (i) and the image of the frame (i+1). The specific region setting unit 110 executes the resetting of the specific region. Si when a feature point of a target object captured at coordinates (x, y) (x=1, 2, ..., Nx; y=1, 2, ..., Ny) in the frame (i) is captured in the frame (i+1) at a different coordinate position that is apart by a threshold value Td or more. Incidentally, a pixel situated at coordinates (x, y) in the frame (i) can change in its pixel value in the next frame (i+1). In this case, if the difference in the pixel value is within a threshold value Tv, it is possible to consider that the point has been captured at the same coordinate position and use the point for the above-described resetting of the specific region Si.

Figure 4:
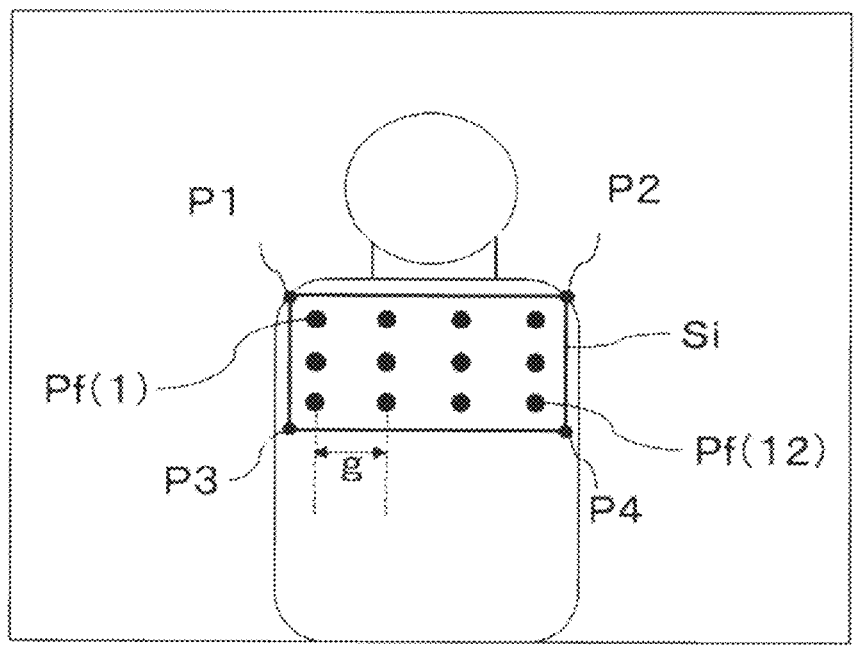
FIG. 4 is an explanatory diagram showing motion vector calculation points.
Figure 5A:
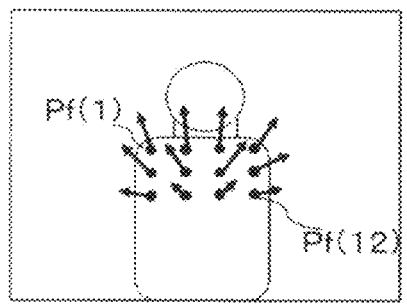
FIGS. 5(a) and 5(b) are schematic diagrams each showing an example of a state of a motion in a breast caused by respiration.
Figure 5B:
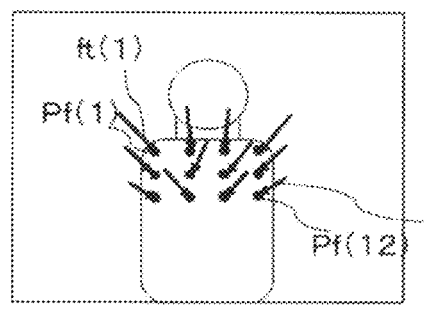

FIG. 4 is an explanatory diagram showing motion vector calculation points. FIG. 5 is an explanatory diagram showing respiration reference axes. The specific region setting unit 110 sets M motion vector calculation points Pf(m) in the specific region Si. Here, m represents an argument that can take an integral value from 1 to M. The motion vector calculation point is a point as the reference of a motion vector. Motion vector calculation points Pf(m) corresponding to the arguments in exist like Pf(1), Pf(2), ..., and Pf(M). For example, motion vector calculation points Pf(m) arranged in three rows and four columns as in FIG. 4 are arranged at even intervals in the specific region Si. The value of M in the example of FIG. 4 is 12. At each motion vector calculation point Pf(m), a motion vector fi(m) in the frame (i) is calculated. Then, a projected motion vector ft(m) is calculated from the motion vector fi(m). The calculation of the projected motion vector ft(m) from the motion vector fi(m) will be described later. Motion vectors fi(m) corresponding to the frame numbers i (i−1, 2, ..., N) exist like f1(m), f2(m), ..., and fN(m). Further, motion vectors fi(m) corresponding to the numerical values in exist like fi(1), fi(2), ..., and fi(M). The following description will be given assuming that the motion vector calculation points Pf(m) are set at intervals g as shown in FIG. 4. Incidentally, the motion vector calculation points Pf(m) do not necessarily have to be set at even intervals but can also be set randomly. The number of motion vector calculation points can be either a plural number or one. Further, it is also possible to make the motion vector calculation unit 120 set the motion vector calculation points Pf(m).

The positions of the motion vector calculation points Pf(m) are set based on the four apices (P1, P2, P3, P4) surrounding the specific region Si, the number M of the motion vector calculation points, and the previously set interval g of the motion vector calculation points Pf(m). If the number M of the motion vector calculation points is large, the motion can be measured more finely, but noise such as a body notion not caused by the respiration becomes more likely to be contained in the measured motion. If the interval g is narrow, the motion can be measured more finely, but noise such as a body motion not caused by the respiration becomes more likely to be contained in the measured motion.

The motion vector calculation unit 120 receives a frame (1), the specific region Si corresponding to the frame (1), and each motion vector calculation point Pf(m) included in the specific region Si, calculates the motion vector fi(m) at each motion vector calculation point Pf(m), and supplies the calculated motion vector fi(m) to the respiration signal calculation unit 140. The following description will be given by using an optical flow.

The motion vector calculation unit 120 calculates the motion vector fi(m) at the motion vector calculation point Pf(m) in the frame (i) based on a movement amount from the coordinate position of the motion vector calculation point Pf(m) in the previous frame (i−1) to the coordinate position of the motion vector calculation point Pf(m) in the frame (i). At every one of the M motion vector calculation points Pf(m), the motion vector fi(m) for N frames is calculated. Here, the method of calculating the motion vector fi(m) is not limited to the optical flow. For example, the Histograms of Oriented Gradients (HOG) feature value may be used.

FIG. 5 is a schematic diagram showing an example of a state of a motion in the breast caused by the respiration. In general, the motion vector fi(m) is calculated in a direction of expanding from the center of the breast at the time of inspiration in the respiration, and calculated in a direction of contracting towards the center of the breast at the time of expiration in the respiration. FIG. 5(*a*) shows a state of the motion in the breast at the time of the inspiration, and FIG. 5(*b*) shows a state of the motion in the breast at the time of the expiration.

For example, when the specific region Si including the breast and the abdomen has been set, the specific region setting unit 110 judges a respiration method, namely, whether the respiration is thoracic respiration or abdominal respiration, by comparing the motion vectors at positions corresponding to the breast and the abdomen. In this case, at least two motion vector calculation points Pf(m) are set at positions where a difference in the motion vector occurs between the breast and the abdomen.

The respiration reference axis calculation unit 130 calculates a respiration central point Pc which is specified as a starting point of the motion caused by the respiration, based on the frame (i). Further, the respiration reference axis calculation unit 130 calculates a straight line extending from the respiration central point Pc towards the motion vector calculation point Pf(m), in which the direction towards the motion vector calculation point Pf(m) is regarded as a positive direction, as a respiration reference axis Rr(m), and supplies the respiration reference axis Rr(m) to the respiration signal calculation unit 140. The respiration reference axis R_(m) is an axis at each motion vector calculation point Pf(m) that is set in a motion direction of the motion vector calculation point Pf(m) caused by the respiration. For example, in the case where the object person is photographed from the direction squarely facing the object person's body when the object person's body is facing forward, it is desirable to photograph the object person so that the respiration reference axes Rr(m) are calculated from a center line of the body to be bilaterally symmetrical.

Figure 6:
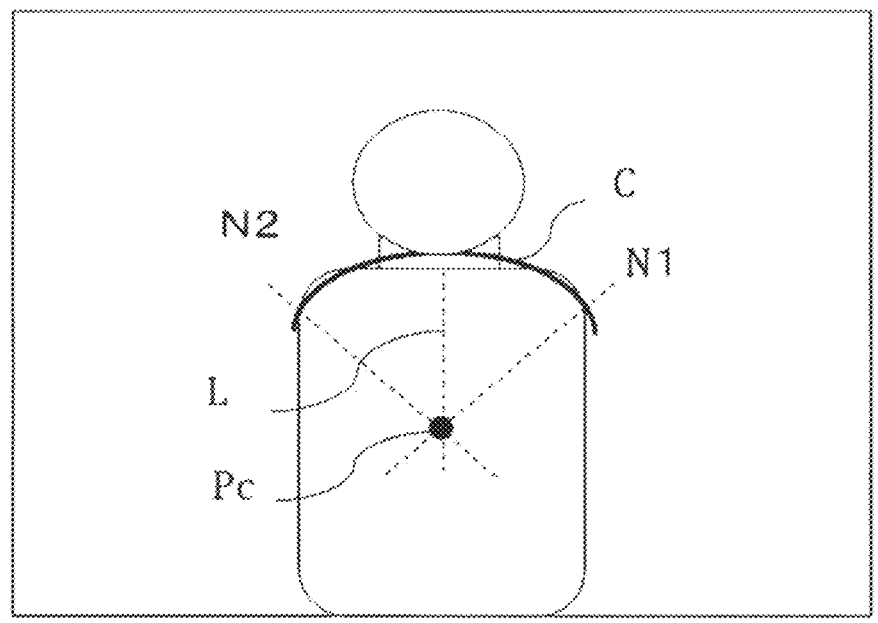
FIG. 6 is a schematic diagram showing an example of a method of calculating a respiration central point.

FIG. 6 is a schematic diagram showing an example of a method of calculating the respiration central point. The respiration reference axis calculation unit 130 calculates the respiration central point Pc as follows, for example: A curved line C approximating an outline of the object person's shoulders so as to overlap with the outline is drawn, and a normal line N1 and a normal line N2 at parts of the curved line C overlapping with end parts of the shoulders are obtained. Incidentally, the normal line N1 is a normal line at a part overlapping with an end part of the left shoulder, and the normal line N2 is a normal line at a part overlapping with an end part of the right shoulder. An intersection point of the normal line N1 and the normal line N2 is determined as the respiration central point Pc. Incidentally, there can be cases where one of the outlines of the shoulders is hardly visible, e.g., hidden behind the seat belt. In such cases, an intersection point of a center line L drawn vertically in a central part of the upper body in regard to the horizontal direction and the normal line N1 or the normal line N2 obtained from the shoulder on the visible side may be determined as the respiration central point Pc. The specific region setting unit 110 executes the resetting of the specific region Si when a feature point of the target object captured at coordinates (x, y) (x=1, 2, . . . , Nx; y=1, 2, . . . , Ny) in the frame (i) is captured in the frame (i+1) at a different coordinate position that is apart by the threshold value Td or more. This is because the specific region Si and the curved line C overlapping with the outline of the shoulders are similarly influenced by the body motion not caused by the respiration. It is also possible to detect straight lines pointing towards the center of a motion by the lungs by using Hough transform and calculate the respiration central point Pc from an intersection point of the straight lines.

Figure 7:
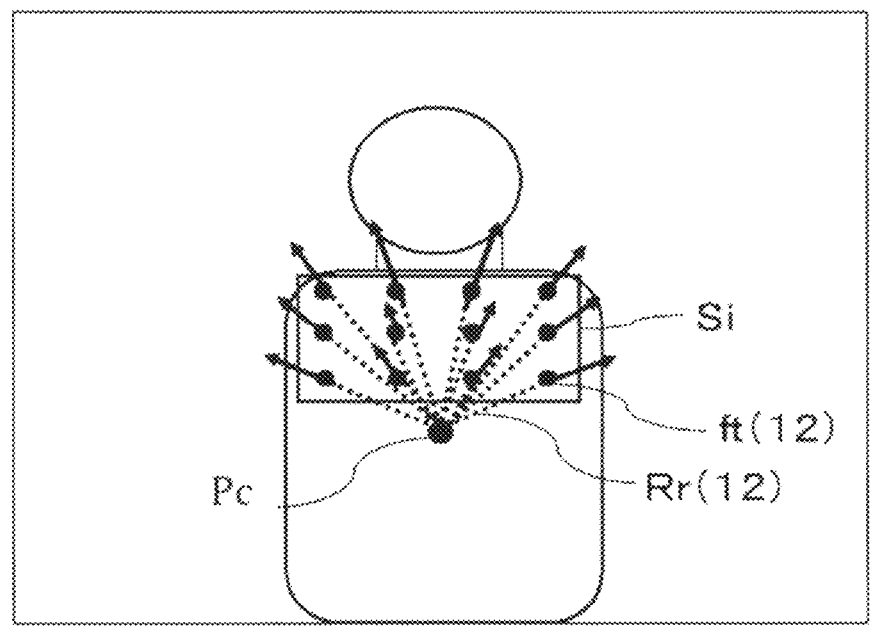
FIG. 7 is an explanatory diagram showing respiration reference axes.

FIG. 7 schematically shows a method of calculating the respiration reference axes Rr(m). The respiration reference axis calculation unit 130 calculates the straight line connecting the respiration central point. Pc and each motion vector calculation point Pf(m), in which the direction from the respiration central point Pc to the calculated motion vector calculation point Pf(m) is regarded as the positive direction, as the respiration reference axis Rr(m). The respiration central point. Pc is a reference point situated in the vicinity of the center of the upper body. Incidentally, in FIG. 7, the respiration reference axis Rr(m) as the straight line connecting the respiration central point Pc and each motion vector calculation point Pf(m) is indicated by a dotted line for the sake of visibility.

Figure 8:
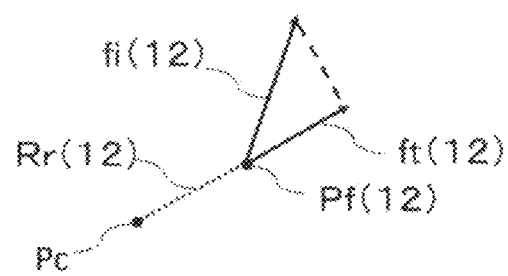
FIG. 8 is a schematic diagram for explaining a method of calculating a projected motion vector from a motion vector based on the respiration reference axis.

FIG. 8 is a schematic diagram for explaining a method of calculating the projected motion vector from the motion vector based on the respiration reference axis. FIG. 8 shows a case where m=12. The motion vector calculation unit 120 calculates the Projected motion vector ft(m) from the calculated motion vector fi(m) and the respiration reference axis Rr(m) calculated by the respiration reference axis calculation unit 130. The respiration signal calculation unit 140 receives the projected motion vector ft(m) from the motion vector calculation unit. 120 and receives the respiration reference axis Rr(m) from the respiration reference axis calculation unit 130. The respiration signal calculation unit 140 calculates a respiration signal Ct(k) from the projected motion vector ft(m) and the respiration reference axis Rr(m). In other words, the respiration signal Ct(k) is calculated from a component of the motion vector in the direction of the respiration reference axis. A respiration signal component F(i) in the frame (i) is obtained by orthogonally projecting the motion vector fi(m) at each motion vector calculation point Pf(m) onto the corresponding respiration reference axis Rr(m) and calculating a sum total of the calculated projected motion vectors ft(m) as in the following expression 1:

$$F(i) = \sum_{m=1}^{M} ft(m) \quad \text{(expression 1)}$$

The respiration signal calculation unit 140 calculates a frame respiration signal Ct(i) indicating the respiration in the frame (i) as Ct(i)=Ct(i−1)+F(i). Incidentally, it is assumed that Ct(0)=0. Further, the respiration signal calculation unit 140 supplies the respiration information calculation unit 150 with a respiration signal $Ct(k)$ indicating transition of the frame respiration signal $Ct(i)$ over N frames. Incidentally, it is also possible to make the respiration signal calculation unit 140 calculate the projected motion vectors $ft(m)$.

Figure 9:
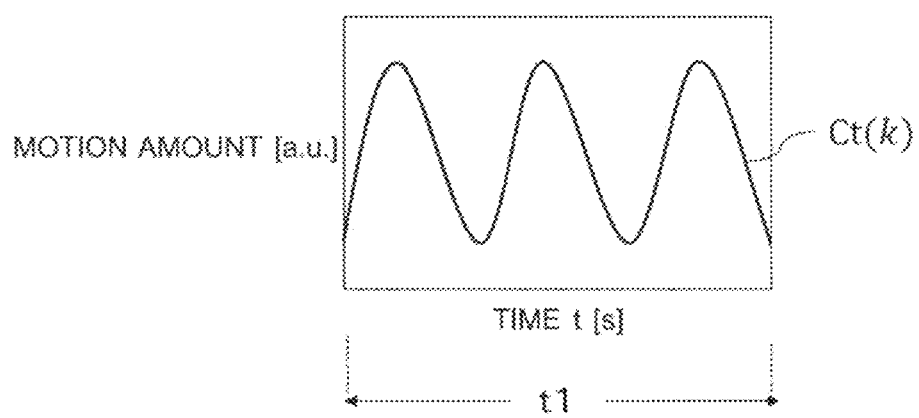
FIG. 9 is a schematic diagram showing an example of a respiration signal outputted at predetermined time intervals.

FIG. 9 is a schematic diagram showing an example of the respiration signal $Ct(k)$ outputted at predetermined time intervals. The horizontal axis in FIG. 9 represents a time t [s] and the vertical axis in FIG. 9 represents a motion amount [a.u.] (a.u.: arbitrary unit). The time t [s] is a time within a predetermined time t1. For example, the respiration signal $Ct(k)$ over N frames at the time t is a waveform signal like the one shown in FIG. 9.

The respiration information calculation unit 150 applies a bandpass filter letting through a frequency range (e.g., 0.1 Hz to 0.5 Hz) corresponding to the respiration to the respiration signal $Ct(k)$ supplied from the respiration signal calculation unit 140. The respiration information estimation result $B(k)$ is calculated from a signal obtained by the filtering and is outputted.

The respiration information estimation result $B(k)$ is, for example, a signal obtained by calculating a breathing rate (bpm: breaths per minute) from the average of a peak interval of the respiration signal $Ct(k)$. Assuming that the average of the peak interval of the respiration signal $Ct(k)$ in FIG. 9 is 3 seconds, the breathing rate is 20 bpm. The respiration information is not limited to the breathing rate but can be a respiration time, an expiration time, an inspiration time, amplitude, a pause time as a time from the expiration to the start of the inspiration, or a ventilation amount. Further, since the frequency range corresponding to the respiration has individual difference depending on the age, sex, etc., a bandpass filter corresponding to the individual difference is used.

Figure 10:
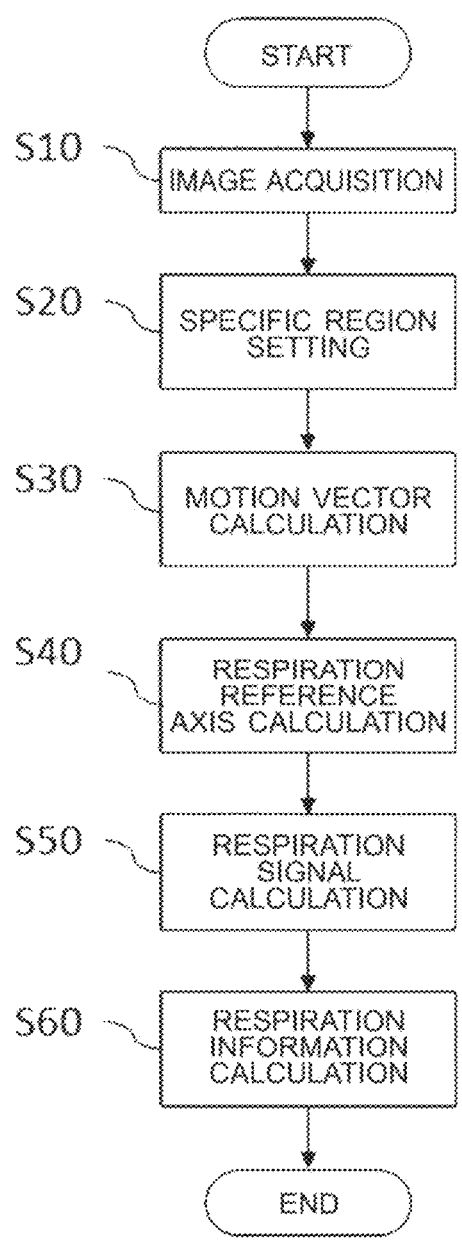
FIG. 10 is a flowchart showing the operation of the respiration information estimation device in the first embodiment.

An operation executed by the respiration information estimation device 100a will be described below. FIG. 10 is a flowchart showing the operation of the respiration information estimation device 100a according to the first embodiment. The flowchart shown in FIG. 10 includes an image acquisition step S10, a specific region setting step S20, a motion vector calculation step S30, a respiration reference axis calculation step S40, a respiration signal calculation step S50 and a respiration information calculation step S60.

In the image acquisition step S10, image data including the upper body of the object person is acquired.

In the specific region setting step S20, the specific region Si of the object person and the motion vector calculation points $Pf(m)$ are set based on the image represented by the acquired image data.

In the motion vector calculation step S30, the motion vectors $fi(m)$ indicating the motion at the M motion vector calculation points $Pf(m)$ set inside the specific region Si are calculated. In the respiration reference axis calculation step S40, the respiration reference axes are calculated from the respiration central point as the starting point of the motion caused by the respiration and the motion vector calculation points.

In the respiration signal calculation step S50, it is calculated the respiration signal $Ct(k)$ indicating the transition of the frame respiration signal $Ct(i)$, obtained by taking the sum total of the projected motion vectors $ft(m)$ as the projection of the M motion vectors $fi(m)$ onto the respiration reference axes $Rr(m)$, over N frames.

In the respiration information calculation step S60, the bandpass filter letting through the frequency range corresponding to the respiration is applied to the respiration signal $Ct(k)$. In the respiration information calculation step S60, the respiration information estimation result $B(k)$ is calculated from the signal after undergoing the filtering.

As described above, according to the first embodiment, the respiration information estimation result of the object person can be calculated with high accuracy even when there is a body motion not caused by the respiration.

In the first embodiment, when motion vector components are projected onto the respiration reference axis $Rr(m)$ by setting the respiration reference axis, a motion vector that does not follow the respiration direction axis due to a body motion takes a small value when projected, and thus the influence of the body motion not caused by the respiration can be reduced and the respiration information estimation result can be calculated with high accuracy.

Second Embodiment

Figure 11:
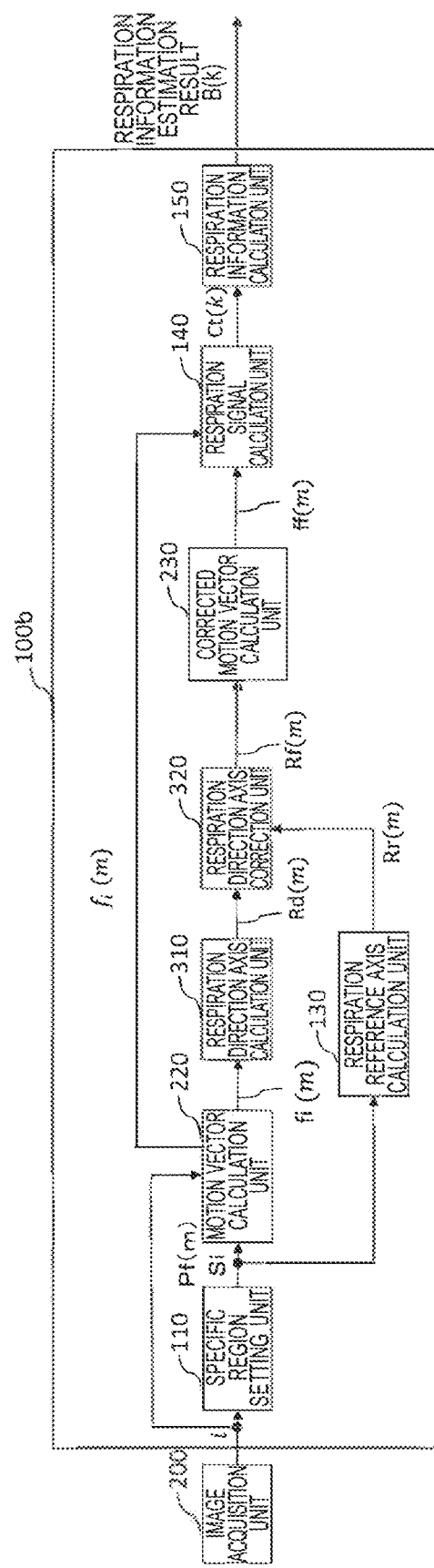
FIG. 11 is a block diagram schematically showing the configuration of a respiration information estimation device in a second embodiment.

FIG. 11 is a block diagram schematically showing the configuration of a respiration information estimation device 100b in a second embodiment. The respiration information estimation device 100b is connected to the image acquisition unit 200 and includes the specific region setting unit 110, a motion vector calculation unit 220, the respiration reference axis calculation unit 130, the respiration signal calculation unit 140, the respiration information calculation unit 150, a respiration direction axis calculation unit 310, a respiration direction axis correction unit 320 and a corrected motion vector calculation unit 230. The specific region setting unit 110, the respiration reference axis calculation unit 130, the respiration signal calculation unit 140 and the respiration information calculation unit 150 of the respiration information estimation device 100b in the second embodiment are respectively the same as the specific region setting unit 110, the respiration reference axis calculation unit 130, the respiration signal calculation unit 140 and the respiration information calculation unit 150 of the respiration information estimation device 100a according to the first embodiment.

The motion vector calculation unit 220 supplies the motion vectors $fi(m)$ to the respiration signal calculation unit 140 and the respiration direction axis calculation unit 310. The motion vector calculation unit 220 differs from the motion vector calculation unit 120 in the first embodiment in that the motion vector calculation unit 120 supplies the motion vectors $fi(m)$ only to the respiration signal calculation unit 140. Incidentally, the respiration information estimation device 100b executes a respiration information estimation method in the second embodiment.

The respiration direction axis calculation unit 310 receives the motion vectors $fi(m)$ for N frames from the motion vector calculation unit 220. At each motion vector calculation point $Pf(m)$, the respiration direction axis $Rd(m)$ is calculated by principal component analysis by using the motion vector $fi(m)$ for 300 frames, for example. Specifically, for each motion vector calculation point $Pf(m)$, variance of the motion vector $fi(m)$ for 300 frames is calculated, and a vector maximizing the variance is calculated as the respiration direction axis $Rd(m)$ at the motion vector calculation point $Pf(m)$. The respiration direction axis calculation unit 310 supplies the respiration direction axis $Rd(m)$ to the respiration direction axis correction unit 320. For example, assuming that the time t1 is 10 seconds and the frame rate r of a camera is 30 frames per second, the motion vector $fi(m)$ for 300 frames is used for the calculation of the respiration direction axis $Rd(m)$.

Figure 12:
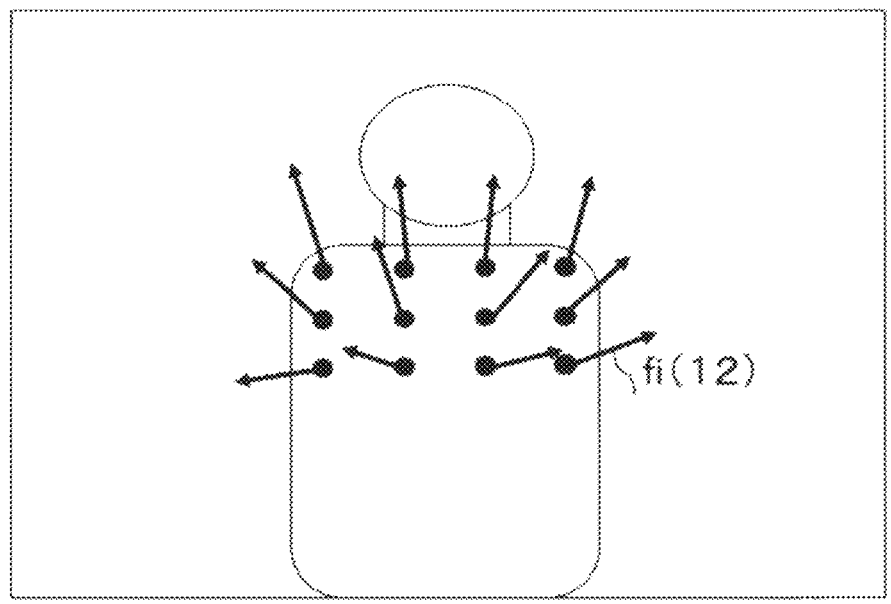
FIG. 12 is an explanatory diagram showing the motion vectors.
Figure 13:
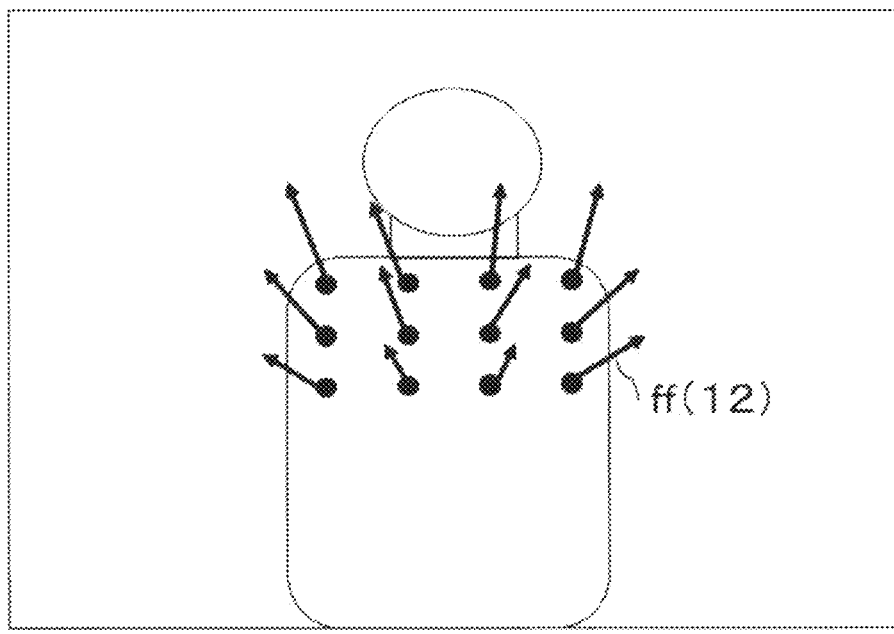
FIG. 13 is an explanatory diagram showing corrected motion vectors.

FIG. 12 is an explanatory diagram showing the motion vectors $fi(m)$. FIG. 13 is an explanatory diagram showing corrected motion vectors ff(m). The value of M in the examples of FIG. 12 and FIG. 13 is 12.

The respiration direction axis correction unit 320 calculates a corrected respiration direction axis by correcting a deviation in the respiration direction axis due to the individual difference based on an angular difference between the respiration reference axis Rr(m) supplied from the respiration reference axis calculation unit 130 and the respiration direction axis Rd(m) supplied from the respiration direction axis calculation unit 310. The respiration direction axis correction unit 320 calculates the corrected respiration direction axis Rf(m) and supplies the corrected respiration direction axis Rf(m) to the corrected motion vector calculation unit 230. The corrected motion vector calculation unit 230 calculates the corrected motion vector ff(m) in a direction along the corrected respiration direction axis Rf(m) and supplies the corrected motion vector ff(m) to the respiration signal calculation unit 140.

Figure 14A:
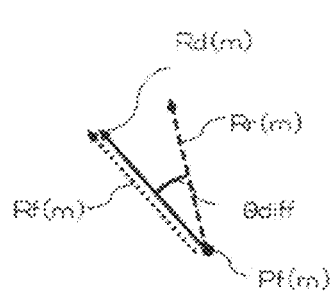
FIGS. 14(a), 14(b) and 14(c) are schematic diagrams for explaining a method of calculating an angular difference between the respiration reference axis and the respiration direction axis and correcting the respiration direction axis by using a predetermined threshold value in the second embodiment.
Figure 14B:
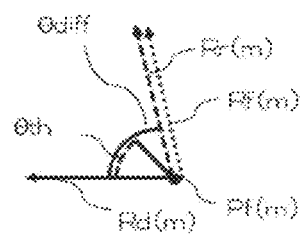
Figure 14C:
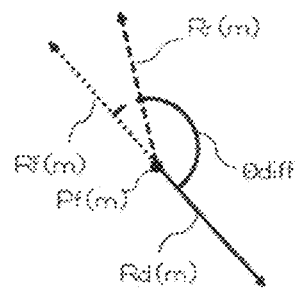

FIG. 14(a) to FIG. 14(c) are schematic diagrams for explaining a method of calculating the angular difference between the respiration reference axis Rr(m) and the respiration direction axis Rd(m) and correcting the respiration direction axis Rd(m) by using a predetermined threshold value. As shown in FIG. 14(a), if the angular difference θdiff between the respiration reference axis Rr(m) and the respiration direction axis Rd(m) at a certain motion vector calculation point Pf(m) is within a threshold value θth, the respiration direction axis Rd(m) is directly handled as the corrected respiration direction axis Rf(m).

As shown in FIG. 14(b), if the angular difference θdiff is greater than the threshold value θth and an angle obtained by subtracting the angular difference θdiff from 180° is greater than the threshold value θth, the respiration direction axis Rd(m) is corrected to the respiration reference axis Rr(m) and handled as the corrected respiration direction axis Rf(m).

As shown in FIG. 14(c), if the angular difference θdiff is greater than the threshold value θth and the angle obtained by subtracting the angular difference θdiff from 180° is less than the threshold value θth, the respiration direction axis Rd(m) is corrected so as to invert its direction by 180° and handled as the corrected respiration direction axis Rf(m).

While the respiration direction axis Rd(m) is corrected to the respiration reference axis Rr(m) in the above description of the case of FIG. 14(b), it is also possible not to use the motion vector calculation point Pf(m) where the angular difference θdiff is greater than the threshold value 9th and the angle obtained by subtracting the angular difference θdiff from 180° is greater than the threshold value θth. Also in FIG. 14(c), unless there is only one motion vector calculation point Pf(m) (i.e., M=1), it is also possible not to use the motion vector calculation point Pf(m) where the angular difference θdiff is greater than the threshold value θth and the angle obtained by subtracting the angular difference θdiff from 180° is less than the threshold value θth.

It is desirable to use the cosine similarity or the like as the method of calculating the angular difference θdiff. Since the cosine similarity is capable of representing angular proximity between vectors, two vectors are approximately in the same direction when the cosine similarity is close to 1, and two vectors are approximately in the opposite directions when the cosine similarity is close to -1. The threshold value θth is desired to be within 45°, for example.

FIG. 15 is a flowchart showing the operation of the respiration information estimation device 100b according to the second embodiment. The flowchart shown in FIG. 15 includes the image acquisition step S10, the specific region setting step S20, the motion vector calculation step S30, the respiration reference axis calculation step S40, a respiration direction axis calculation step S41, a respiration direction axis correction step S42, a corrected motion vector calculation step S43, the respiration signal calculation step S50 and the respiration information calculation step S60.

The image acquisition step S10, the specific region setting step S20, the motion vector calculation step S30, the respiration reference axis calculation step S40, the respiration signal calculation step S50 and the respiration information calculation step S60 in the respiration information estimation device 100b according to the second embodiment are respectively the same as the image acquisition step S10, the specific region setting step S20, the motion vector calculation step S30, the respiration reference axis calculation step S40, the respiration signal calculation step S50 and the respiration information calculation step S60 in the respiration information estimation device 100a according to the first embodiment.

In the respiration direction axis calculation step S41, the respiration direction axis Rd(m) is calculated from the motion vector fi(m) for a plurality of consecutive frames.

In the respiration direction axis correction step S42, the corrected respiration direction axis Rf(m) is calculated by making the correction of the respiration direction axis Rd(m) depending on the relationship between the respiration reference axis Rr(m) and the respiration direction axis Rd(m).

In the corrected motion vector calculation step S43, the corrected motion vector ff(m) in the direction along the corrected respiration direction axis Rf(m) is calculated.

As described above, with the respiration information estimation device 100b according to the second embodiment, by calculating the respiration direction axis Rd(m), the decrease in the accuracy caused by the deviation in the respiration reference axis Rr(m) due to the individual difference can be reduced, the influence of the body motion not caused by the respiration can be reduced, and the respiration information estimation result can be calculated with higher accuracy.

Incidentally, in the above description, the respiration direction axis Rd(m) is directly handled as the corrected respiration direction axis Rf(m) if the angular difference θdiff between the respiration direction axis Rd(m) and the respiration reference axis Rr(m) at the motion vector calculation point Pf(m) is within the threshold value θth, and the respiration direction axis Rd(m) is corrected to the respiration reference axis Rr(m) and handled as the corrected respiration direction axis Rf(m) if the angular difference θdiff is greater than or equal to the threshold value θth. However, it is also possible to exclusively use the projected motion vectors at motion vector calculation points Pf(m) where the angular difference θdiff is within the threshold value θth for the calculation of the respiration signal component F(i).

Third Embodiment

Figure 16:
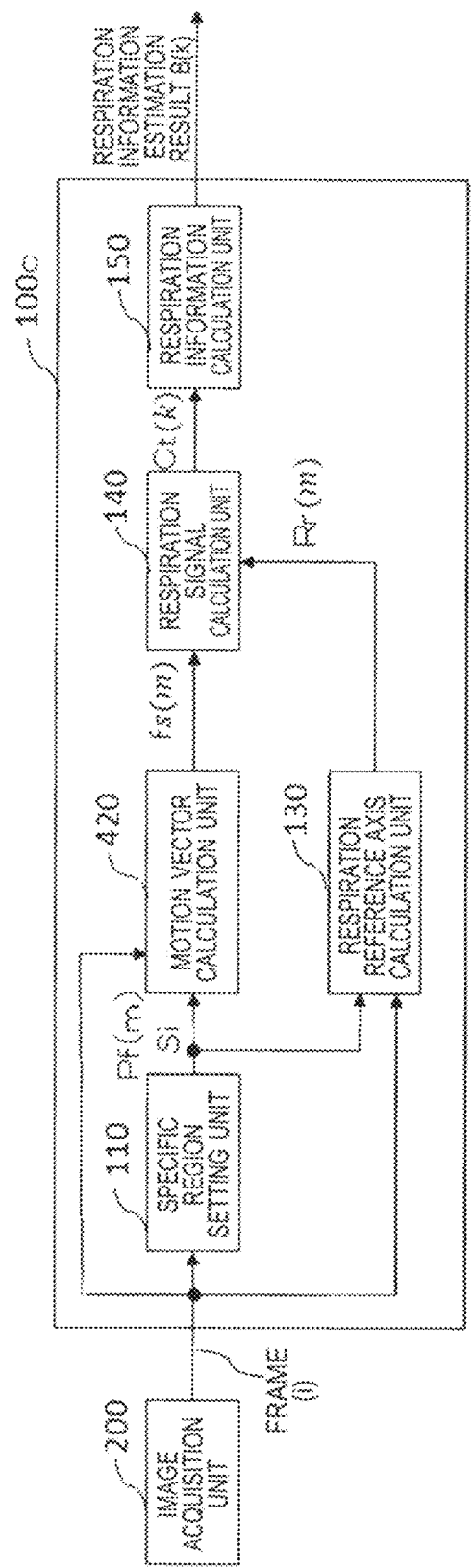
FIG. 16 is a block diagram schematically showing the configuration of a respiration information estimation device in a third embodiment.

FIG. 16 is a block diagram schematically showing the configuration of a respiration information estimation device 100c according to a third embodiment. The respiration information estimation device 100c is similar to the specific region setting unit 110, the respiration reference axis calculation unit 130, the respiration signal calculation unit 140 and the respiration information calculation unit 150 of the respiration information estimation device 100a according to the first embodiment. However, a motion vector calculation unit 420 has a configuration different from the motion vector calculation unit 120 in the first embodiment. Incidentally, the respiration information estimation device 100c executes a respiration information estimation method as an information processing method according to, the third embodiment.

FIG. 17 is a block diagram schematically showing the configuration of the motion vector calculation unit 420 in the third embodiment. The motion vector calculation unit 420 includes a motion component calculation unit 420a, a non-respiration component calculation unit 420b and a respiration component calculation unit 420c.

Similarly to the motion vector calculation unit 120 in the first embodiment, the motion component calculation unit. 420a receives the frame (i), the specific region Si and the motion vector calculation points Pf(m), calculates the motion vector fi(m) at each motion vector calculation points Pf(m), and supplies the motion vector fi(m) to the respiration component calculation unit 420c.

The non-respiration component calculation unit 420h calculates a non-respiration component di(q) from a region outside the specific region. Si. The number q is an integer greater than or equal to 1 representing a point where the non-respiration component is calculated, and the integer q is set arbitrarily. The total number of the points where the non-respiration component is calculated is u. The non-respiration component calculation unit 420b supplies the respiration component calculation unit 420c with an average value d_avei ($=\Sigma di(q)/u$) of the non-respiration components di(q) calculated from a plurality of points for u. While the non-respiration components di(q) are calculated from a plurality of points and the average value d_avei of the non-respiration components is obtained in the above description, it is also possible to obtain the non-respiration component di(q) from one point.

The respiration component calculation unit 420c calculates a respiration component fs(m) (fi(m)=d_avei) from the motion vector fi(m) supplied from the motion component calculation unit 420a and the average value d_avei of the non-respiration components supplied from the non-respiration component calculation unit 420b.

FIG. 18 is a schematic diagram showing a method of removing the average value d_avei of the non-respiration components from the motion vector fi(m). For the desired respiration component fs(m) shown in FIG. 18(*a*), the average value d_avei of the non-respiration components such as a body motion like that shown in FIG. 18(*b*) is calculated and is removed by performing an operation with the motion vector fi(m) as shown in FIG. 18(*c*). For example, the non-respiration components di(q) are calculated in the region surrounded by the dotted line frame where a motion caused by the respiration does not occur, and the average value d_avei of the non-respiration components is calculated. Accordingly, the respiration component fs(m) is calculated by taking the difference between the motion vector fi(m) of the specific region Si and the average value d_avei of the non-respiration components and is supplied to the respiration signal calculation unit 140.

As described above, with the respiration information estimation device 100c according to the third embodiment, the respiration component can be calculated by calculating the average value d_avei of the non-respiration components and taking the difference between the motion vector fi(m) and the average value d_avei, and respiration information estimation that is robust to motions can be executed. Accordingly, in the third embodiment, the respiration information estimation result can be calculated with higher accuracy.

In the respiration information estimation device configured as above, in cases like when the upper body of the object person in the captured image of the object person is hard to recognize, the respiration information estimation result may be calculated by identifying the object person and using the respiration central point or the like at the time when the object person was previously identified.

Further, while the image data used for outputting the respiration information estimation result B(k) is described as image data of video including a total of N frames captured at a predetermined frame rate r in the above description, the image data used for outputting the respiration information estimation result B(k) is not limited to such image data; consecutive N1 frames among the N frames, for example, may be specified as the image data used for outputting the respiration information estimation result B(k).

Figure 19:
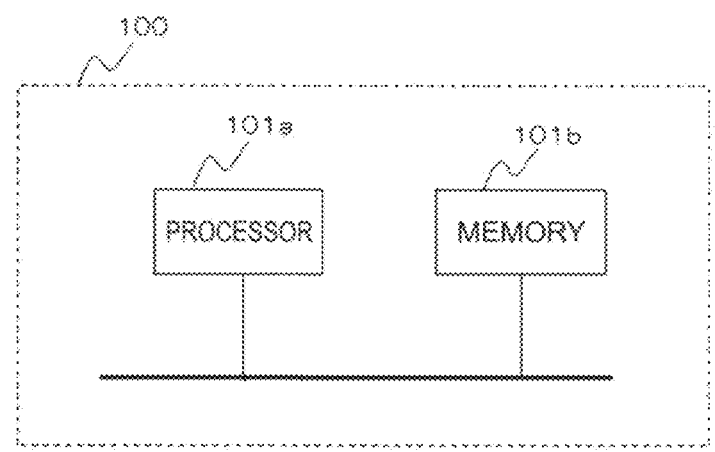
FIG. 19 is a diagram showing an example of the hardware configuration of the respiration information estimation device in the third embodiment.
Figure 20:
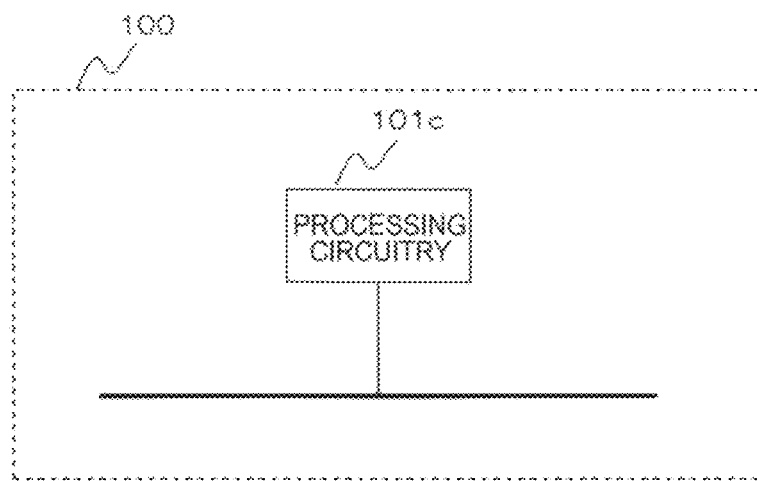
FIG. 20 is a diagram showing another example of the hardware configuration of the respiration information estimation device in the third embodiment.

FIG. 19 is a diagram showing an example of the hardware configuration of the respiration information estimation device 100 (100a, 100b, 100c), FIG. 20 is a diagram showing another example of the hardware configuration of the respiration information estimation device 100.

The respiration information estimation device 100a is formed with at least one processor 101a and a memory 101b, for example. The processor 101a is a central processing unit (CPU) that executes a program stored in the memory 101b, for example. In this case, the functions of the respiration information estimation device 100 are implemented by software, firmware, or a combination of software and firmware. The software and the firmware are stored in the memory 101b as programs. With this configuration, a program for implementing the functions of the respiration information estimation device 100 (e.g., the respiration information estimation method described in the embodiments) is executed by a computer.

The memory 101b is a computer-readable record medium, such as a volatile memory like a Random Access Memory (RAM) or a Read Only Memory (ROM), a nonvolatile memory, or a combination of a volatile memory and a nonvolatile memory.

The respiration information estimation device 100 may also be famed with a processing circuitry 101c as dedicated hardware such as a single circuit or a combined circuit. In this case, the functions of the respiration information estimation device 100 are implemented by the processing circuitry 101c.

While embodiments of the present disclosure have been described as above, the present disclosure is not limited to these embodiments.

DESCRIPTION OF REFERENCE CHARACTERS

200: image acquisition unit, 100a, 100b, 100c: respiration information estimation device, 110: specific region setting unit, 120, 320: motion vector calculation unit, 130: respiration reference axis calculation unit, 140: respiration signal calculation unit, 150: respiration information calculation unit, 420a: motion component calculation unit, 420b: non-respiration component calculation unit, 420c: respiration component calculation unit

What is claimed is:

1. A respiration information estimation device comprising:
    a specific region setting circuitry to set a specific region and a motion vector calculation point as a point as a reference of a motion vector based on an image including an upper body of an object person;
    a respiration reference axis calculating circuitry to detect straight lines pointing towards a center of a motion by the lungs of the object person, calculate a respiration central point from an intersection point of the straight lines, and calculate a straight line extending from the respiration central point towards the motion vector calculation point as a respiration reference axis;

a motion vector calculating circuitry to calculate the motion vector from a movement amount of the motion vector calculation point in each of the images captured consecutively;

a respiration signal calculating circuitry to calculate a respiration signal from a component of the motion vector in a direction of the respiration reference axis; and a respiration information calculating circuitry to calculate a respiration information estimation result, as a result of estimating a body motion caused by the respiration, from the respiration signal.

2. The respiration information estimation device according to claim 1, wherein the respiration reference axis calculating circuitry calculates an intersection point of a normal line at a part of a curved line, approximating an outline of the object person's shoulders so as to overlap with the outline, overlapping with an end part of a right shoulder and a normal line at a part of the curved line overlapping with an end part of a left shoulder as the respiration central point and calculates a vector heading from the respiration central point towards the motion vector calculation point as the respiration reference axis.

3. The respiration information estimation device according to claim 1, wherein the respiration reference axis calculating circuitry calculates an intersection point of a normal line at a part of a curved line, approximating an outline of the object person's shoulders so as to overlap with the outline, overlapping with an end part of a right shoulder or a left shoulder and a center line drawn vertically in a central part of the upper body of the object person in regard to a horizontal direction as the respiration central point and calculates a vector heading from the respiration central point towards the motion vector calculation point as the respiration reference axis.

4. The respiration information estimation device according to claim 1, wherein
the specific region setting circuitry sets a plurality of the motion vector calculation points in the specific region,
the respiration reference axis calculating circuitry calculates the respiration reference axis at each of the motion vector calculation points,
the motion vector calculating circuitry calculates a projected motion vector as a component in the direction of the respiration reference axis from the motion vector calculated at each of the motion vector calculation points, and
the respiration signal calculating circuitry calculates a sum total of the projected motion vectors as a frame respiration signal and calculates the respiration signal indicating transition of the frame respiration signal regarding each image over a plurality of the images.

5. The respiration information estimation device according to claim 1, wherein the respiration information calculating circuitry calculates the respiration information estimation result by applying a bandpass filter corresponding to a frequency of the respiration to the respiration signal.

6. The respiration information estimation device according to claim 1, wherein the motion vector calculating circuitry calculates a motion component in a region where a motion caused by the respiration does not occur as a non-respiration component and calculates a respiration component by taking a difference between a motion component in the specific region and an average value of the non-respiration component.

7. The respiration information estimation device according to claim 1, wherein the specific region is identified based on identification of a face of the object person.

8. The respiration information estimation device according to claim 7, wherein the specific region setting circuitry:
detects a facial quadrangular region of the face,
calculates a specific region height and width, and
sets the specific region below the detected facial region at a point based on the specific region heigh and width.

9. A respiration information estimation device comprising:
a specific region setting circuitry to set a specific region based on an image including an upper body of an object person;
a motion vector calculating circuitry to calculate a motion vector from a movement amount of a motion vector calculation point, as a point as a reference of the motion vector, in each of the images captured consecutively;
a respiration direction axis calculating circuitry to calculate a respiration direction axis by principal component analysis by using the motion vector;
a respiration reference axis calculating circuitry to detect straight lines pointing towards a center of a motion by the lungs of the object person, calculate a respiration central point from an intersection point of the straight lines, and calculate a straight line extending from the respiration central point towards the motion vector calculation point as a respiration reference axis;
a respiration direction axis correcting circuitry to calculate a corrected respiration direction axis by correcting a deviation in the respiration direction axis due to an individual difference based on an angular difference between the respiration reference axis and the respiration direction axis;
a corrected motion vector calculating circuitry to calculate a corrected motion vector in a direction along the corrected respiration direction axis;
a respiration signal calculating circuitry to calculate a respiration signal from a component of the corrected motion vector in a direction of the respiration reference axis; and
a respiration information calculating circuitry to calculate a respiration information estimation result, as a result of estimating a body motion caused by the respiration, from the respiration signal.

10. The respiration information estimation device according to claim 9, wherein the corrected respiration direction axis is set at the respiration direction axis if the angular difference between the respiration reference axis and the respiration direction axis at the motion vector calculation point is within a predetermined threshold value, the corrected respiration direction axis is set at the respiration reference axis if the angular difference is greater than the predetermined threshold value and an angle obtained by subtracting the angular difference from 180° is greater than the threshold value, and the corrected respiration direction axis is set at an axis obtained by inverting a direction of the respiration direction axis by 180° if the angular difference is greater than the predetermined threshold value and the angle obtained by subtracting the angular difference from 180° is less than the threshold value.

11. A respiration information estimation method comprising:

setting a specific region and a motion vector calculation point as a point as a reference of a motion vector based on an image including an upper body of an object person;
detecting straight lines pointing towards a center of a motion by the lungs of the object person;
calculating a respiration central point from an intersection point of the straight lines;
calculating a straight line extending from the respiration central point towards the motion vector calculation point as a respiration reference axis;
calculating the motion vector from a movement amount of the motion vector calculation point in each of the images captured consecutively;
calculating a respiration signal from a component of the motion vector in a direction of the respiration reference axis; and
calculating a respiration information estimation result, as a result of estimating a body motion caused by the respiration, from the respiration signal.

* * * * *